United States Patent
Chong et al.

[19]

[11] Patent Number: 6,093,163
[45] Date of Patent: Jul. 25, 2000

[54] DEVICE FOR HALLUX VALGUS

[76] Inventors: Andrew K. Chong; Catherine S. Chong, both of 501 E. Praire Ave., Wheaton, Ill. 60187

[21] Appl. No.: 09/274,084

[22] Filed: Mar. 22, 1999

[51] Int. Cl.[7] .................................................. A61F 5/00
[52] U.S. Cl. .............................. 602/30; 602/60; 602/61
[58] Field of Search ........................... D24/192; 128/880, 128/882, 892, 893, 894; 602/5, 20, 21, 22, 30, 60, 61, 66

[56] References Cited

U.S. PATENT DOCUMENTS

| | | | |
|---|---|---|---|
| 1,746,865 | 2/1930 | Page .......................................... | 602/30 |
| 2,572,152 | 10/1951 | Horlacher .................................. | 602/30 |
| 2,958,324 | 11/1960 | Berkeman . | |
| 4,632,103 | 12/1986 | Fabricant et al. ......................... | 602/30 |
| 4,644,940 | 2/1987 | Nakamura . | |
| 4,729,369 | 3/1988 | Cook . | |
| 4,856,505 | 8/1989 | Shaffer . | |
| 4,940,046 | 7/1990 | Jacoby ...................................... | 602/30 |
| 5,453,083 | 9/1995 | Kahahara .................................. | 602/30 |
| 5,933,863 | 10/1999 | Monsue ..................................... | 2/21 |

OTHER PUBLICATIONS

Donatto, et al Custom Molded Orthotics in Post Operative Hellux Valgus Immobilisation Orthopedics, vol. 15 #4, Apr. 1992.
Lieberson, et al. Congenital Hallux Valgus Orthopedics May 1991 vol. 14 #5.
Berkemann Catalog—Post –Op. Bunion Soft Splint™ (p. 4), Post –Op –Right Splint ( p. 4), Bunion Day Splint ( p. 5 )
Darco Toe—Alignment Splint ( p. 6 ).

*Primary Examiner*—Kim M. Lee

[57] ABSTRACT

A unitary device for the correction of hallux valgus is made of an elastomeric fabric material that includes a large portion that encloses the forefoot cirumferentially, and a smaller portion that encloses the great toe circumferentially. The fabric for constructing the device is cut in such a way that there is a bias towards varus of the great toe. Once the device is applied on the great toe and forefoot, the bias of the cut exerts a varus force on the great toe, thus correcting the valgus deformity.

1 Claim, 2 Drawing Sheets

DEVICE FOR HALLUX VALGUS

BACKGROUND OF THE INVENTION

Hallux valgus is a deformity of the foot characterized by lateral deviation of the great toe with medial deviation of the first metatarsal bone. This often leads to irritation of the bursal sac on the medial side of the metatarsophalangeal joint with thickening and pain (the bunion).

The condition may develop in childhood, but often does not start to cause symptoms until middle age. It is probably hereditary, but often aggravated by inappropriate shoewear.

When the deformity is severe and causes symptoms, the treatment is often surgery to correct the hallux valgus and excision of the bunion.

Splints and braces have been used for conservative treatment to prevent the deformity from getting worse, as well as for postoperative wear to prevent recurrence. Splints and braces fall into the following categories:

1) Rigid splints which may be custom-molded or ready made. Custom-molded rigid splints are usually made of a thermoplastic that is molded to the medial aspect of the foot and great toe. The foot and great toe are then strapped to the splint by means of hook and loop fasteners. Examples are Donatto et al (Orthopedics Vol. 15, No. 4, 1992) and Lieberson et al (Orthopedics, Vol. 14, No. 5, 1991), and Cook (U.S. Pat. No. 4,729,369 in 1988). Ready-made braces are usually an unmolded straight splint made of plastic or metal against which the foot and great toe are attached. Examples are Shaffer (U.S. Pat. No. 4,856,505 in 1988), and Darco (Berkemann catalog—page 6).

Another example of a rigid splint is Berkemann (U.S. Pat. No. 2,958,324 in 1960) which consists of a rigid toe splint connected to a fulcrum on the foot, the other arm connected proximally to an elastic band. The elastic band through the fulcrum will bias the great toe into a varus position. A refinement is now manufactured by Berkemann Co. (Catalog—page 4), but the principle remains the same.

2) Flexible braces are made of fabric material that circumferentially covers the forefoot and great toe. Correction is obtained by use of a strap that is attached to the brace by means of hook and loop fasteners that pulls the great toe into the corrected position. Nakamura (U.S. Pat. No. 4,644,940 in 1987) has a strap that crisscrosses the foot to obtain the varus pull on the great toe. Both Fabricant (U.S. Pat. No. 4,632,103 in 1986) and Berkemann's bunion day-splint describe a strap that extends from the great toe along the medial aspect of the foot and around the heel, ending on the anterolateral aspect of the foot onto which it is attached. Jacoby (U.S. Pat. No. 4,940,046 in 1990) has a strap that extends from the lateral aspect of the great toe across the top of the metatarsophalangeal joint of the great toe to the medial aspect of the foot.

The braces that are available on the market at this time have the following disadvantages:

1. The rigid braces including the Berkemann toe straightening device (U.S. Pat. No. 2,958,324 in 1960, and Berkemann catalog—page 4), made of thermoplastic or metal are bulky and uncomfortable to wear. They are usually worn only at night since it is difficult to walk in them.
2. The flexible braces can be worn in shoes. However the use of straps with hook and loop fasteners placed over the fabric of the brace add considerably to the bulk of the contraption, and are very difficult to fit in regular shoes. Extra width or depth shoes are usually needed. The Nakamura and Jacoby braces use straps with hook and loop fasteners. With constant walking in the brace, the hook and loop fastener loosens, and correction is lost. Constant readjustment through the day is needed to keep the strap taut to maintain correction. The Berkemann bunion day-splint consists of a midfoot binder that compresses the midfoot, and a separate toe sock that is attached by a strap that is pulled around the back of the heel. The toe sock is placed on the great toe, and the strap pulls the great toe into the corrected position. The strap may be an elastic or inelastic band, but the principle is the same. The correction is obtained by pulling the great toe and holding it in position, by winding the strap around the back of the heel. This causes pressure on the heel and skin irritation around the heel.

Hence there is still a great need for a device that accomplishes all of the following:

1) Ease of applying and removing
2) Correction of the hallux valgus without adding so much bulk, so that it is comfortable even in a regular shoe
3) Consistent corrective force on the hallux valgus that is not lost as the brace is worn through the day, and that does not require repeated adjustment to obtain continued correction
4) Does not put pressure on the heel and cause heel irritation.

BRIEF SUMMARY OF THE INVENTION

The present invention seeks to overcome the disadvantages of the hallux valgus braces available at this time, and accomplishes all the objectives enumerated above.

The invention is a flexible unitary device made of flexible elastomeric material (such as neoprene fabric) which includes a large portion that encloses the forefoot circumferentially and a small portion that encloses the great toe circumferentially.

The device does not use straps or hook and loop fasteners to effect correction of the lateral deviation of the great toe. The elastomeric fabric used for constructing the device is cut in such a way that when applied on the foot, there is a bias towards varus (medial deviation) of the great toe, thus correcting the hallux valgus deformity.

DETAILED DESCRIPTION OF THE INVENTION

The following description pertains to the right foot.

Figure 3A:
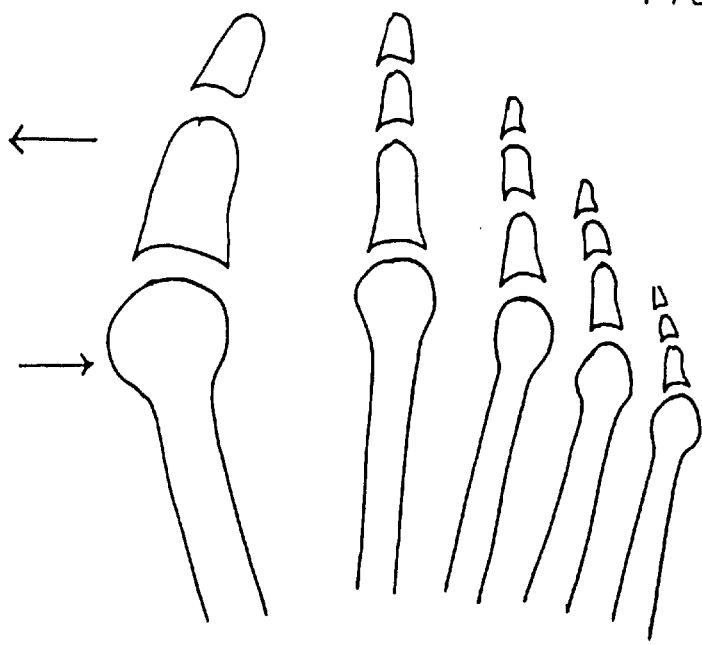
FIG. 3A shows the top plan view of the foot with hallux valgus.

The device is designed to correct hallux valgus deformity by providing a compressive force on the forefoot to correct the medial deviation of the first metatarsal bone, and a varus force on the great toe to correct the valgus deviation of the great toe, as shown in FIG. 3A.

Figure 1:
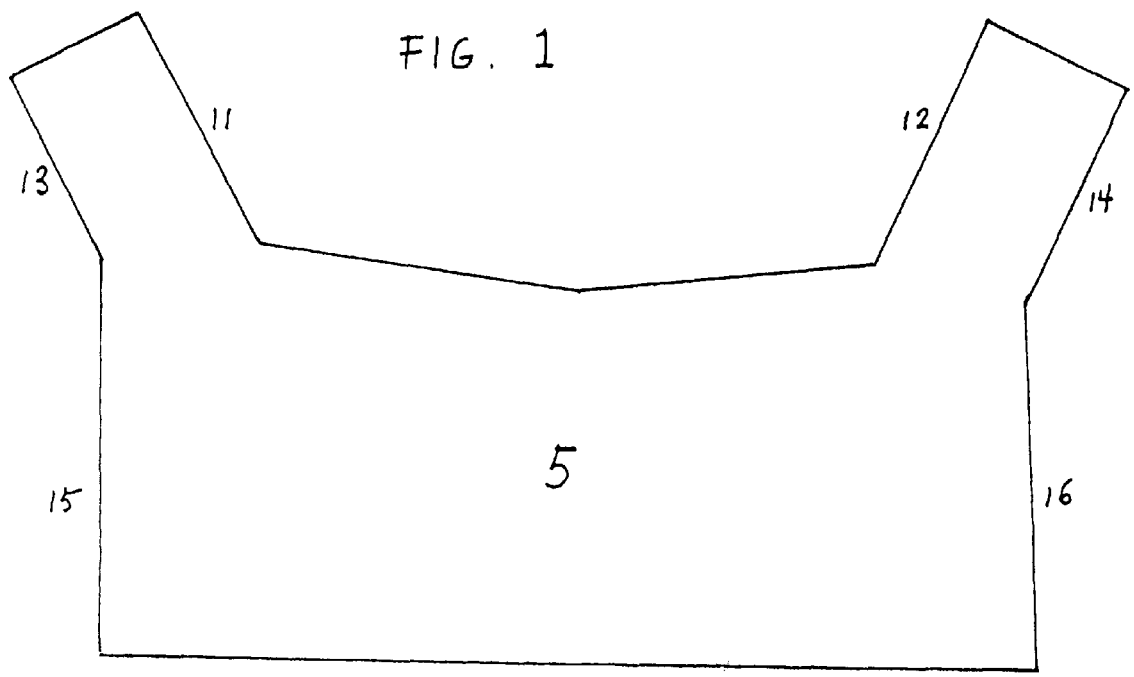
FIG. 1 is a front plan view of the neoprene fabric cut to shape and laid flat, ready for the longitudinal edges to be joined together.
Figure 2:
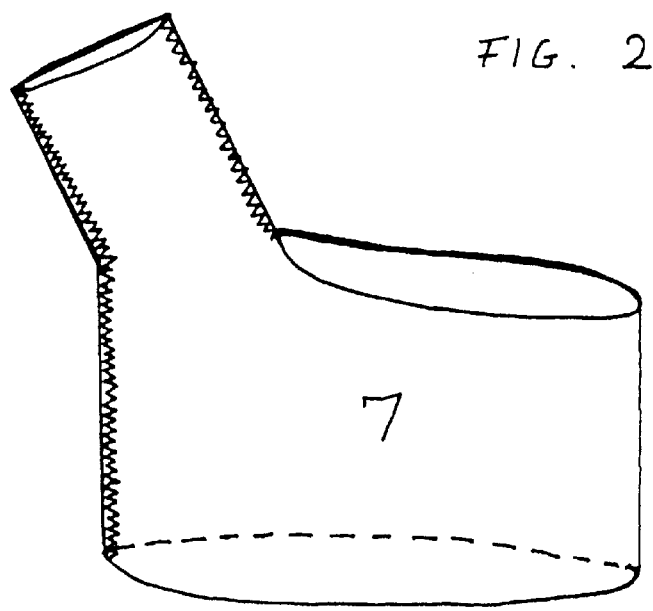
FIG. 2 is a perspective view of the neoprene fabric with longitudinal edges joined together to form a tubular structure.

FIG. 1 shows a neoprene fabric 5 (2 to 3 mm. thickness) cut to the shape shown, such that the angle of the cut formed by edges 13 and 15 is identical to the angle formed by edges 14 and 16. The dimensions defined by edges 13 and 15 are identical to the dimensions defined by edges 14 and 16, and the dimensions defined by edge 11 are identical to the dimensions defined by edge 12; in other words, mirror images. When edge 11 is joined to edge 12, edge 13 is joined to edge 14, and edge 15 is joined to edge 16 by sewing, a unitary tubular structure 7 is obtained which could be pulled over a foot, that encloses the great toe and forefoot circumferentially as in FIG. 2. Notice that the thickness and amount of fabric used and the dimensions of the cut is determined by the size of the foot, so as to obtain a snug fit. Also, it should be noted that the angle formed by edges 13 and 15, and edges 14 and 16 can be varied, depending on the magnitude of varus bias required.

Figure 3B:
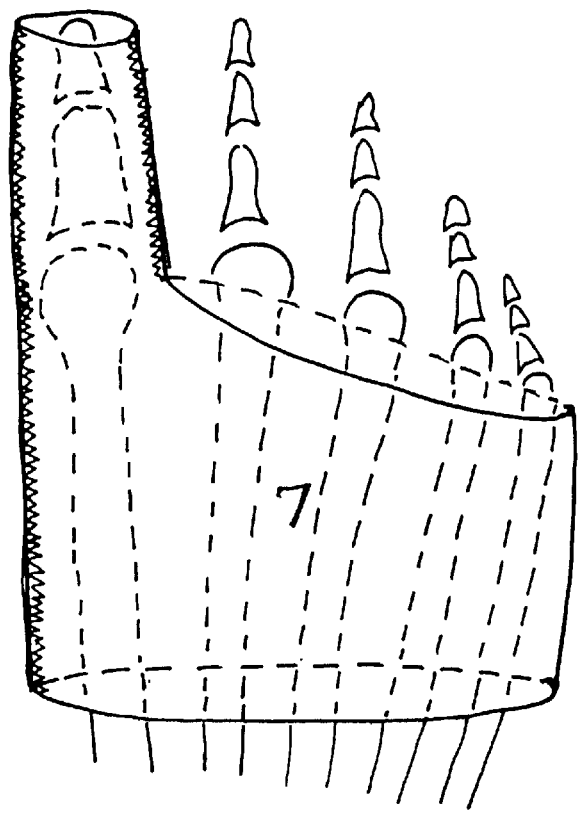
FIG. 3B shows the top plan view of the foot with corrective device applied, showing correction of the hallux valgus deformity.

FIG. 3A shows the top plan view of the skeleton of the right forefoot and toes, showing hallux valgus. FIG. 3B shows device 7 applied onto the foot with hallux valgus. The hallux valgus deformity is now counteracted by the varus bias of the toe portion of device 7, pulling the great toe into a more neutral position.

Thus the device described provides a convenient, comfortable and effective means of controlling hallux valgus. It corrects the lateral deviation of the great toe without significantly adding to the bulk of the neoprene fabric, so that it is comfortable even when worn in a regular shoe. It does not have a strap that goes around the back of the heel and causes heel irritation, and it does not use hook and loop fasteners that necessitate frequent readjustments during wear.

While the above description contains many specificities, these should not be construed as limitations on the scope of the invention, but rather as an exemplification of one preferred embodiment thereof For example, any elastomeric material other than neoprene may be used. Other ways of cutting the fabric may be used, e.g., edges 13 and 15 as well as edges 14 and 16 may be curvilinear cuts rather than angular cuts. As long as the construction results in a tubular structure as illustrated in FIG. 3, the result is the same.

Accordingly, the scope of the invention should be determined not by the embodiment(s) illustrated, but by the appended claims and their legal equivalents.

What is claimed is:

1. A unitary device for hallux valgus consisting of
   a flexible elastomeric fabric material that has a large portion adapted to enclose the forefoot circumferentially, and a small portion adapted to enclose the great toe circumferentially during use,
   wherein the fabric material is cut in such a way that the toe portion has a bias towards varus.

* * * * *